US008252066B2

(12) United States Patent
Haun

(10) Patent No.: US 8,252,066 B2
(45) Date of Patent: Aug. 28, 2012

(54) PYRAMID RECEPTACLE FOR COUPLING A PROSTHETIC LIMB TO A SOCKET

(76) Inventor: Dennis G. Haun, Fallston, MD (US)

( * ) Notice: Subject to any disclaimer, the term of this patent is extended or adjusted under 35 U.S.C. 154(b) by 109 days.

(21) Appl. No.: 12/942,590

(22) Filed: Nov. 9, 2010

(65) Prior Publication Data
US 2011/0112657 A1    May 12, 2011

Related U.S. Application Data

(60) Provisional application No. 61/281,033, filed on Nov. 12, 2009.

(51) Int. Cl.
*A61F 2/80* (2006.01)
*A61F 2/60* (2006.01)

(52) U.S. Cl. ......................................................... 623/38
(58) Field of Classification Search .................... 623/27, 623/28, 38
See application file for complete search history.

(56) References Cited

U.S. PATENT DOCUMENTS

| 3,906,552 | A | * | 9/1975 | Weber | 623/47 |
| 5,571,192 | A | * | 11/1996 | Schonhoffer | 623/17.11 |
| 5,800,562 | A | * | 9/1998 | Wilkinson | 623/27 |
| 7,189,264 | B2 | * | 3/2007 | Curtis | 623/27 |
| 2006/0095140 | A1 | * | 5/2006 | Steinbarger et al. | 623/38 |

* cited by examiner

*Primary Examiner* — Bruce E Snow
(74) *Attorney, Agent, or Firm* — Ober, Kaler, Grimes & Shriver; Royal W. Craig

(57) ABSTRACT

A pyramid receptacle for coupling a prosthetic limb to a socket, comprising a unitary machined component formed with an externally-threaded neck section flanged by a larger-diameter disk. The disk is formed with a concave face, and a central cavity. A plurality of threaded set screws are journalled into the hollow threaded neck section through the threads thereof and into communication with the central cavity. Machining the threaded holes for the plurality of set screws directly through the hollow threaded neck section, and ensuring that the set screws stay flush or recessed when fully tightened effectively halves the length of the pyramid receptacle and facilitates angular adjustment of the prosthetic limb before affixing it in place, but does not significantly increase the profile length of the interconnection between socket and knee joint.

14 Claims, 5 Drawing Sheets

PYRAMID RECEPTACLE FOR COUPLING A PROSTHETIC LIMB TO A SOCKET

CROSS-REFERENCE TO RELATED APPLICATION(S)

The present application derives priority from U.S. provisional patent application Ser. No. 61/281,033 filed Nov. 12, 2009.

BACKGROUND OF THE INVENTION

1. Field of the Invention

The present invention relates to prosthetics and, more particularly, to a prosthetic-limb coupling-socket adapter assembly that affords angular adjustment for the prosthetic limb, yet does not significantly increase the profile length of the interconnection between socket and knee or foot joint for amputation patients.

2. Description of the Background

There are a variety of different types of prosthetic devices for patients that have had either transfemoral (above-knee) or transtibial (below the knee) amputation. A typical transfemoral prosthetic device consists of a custom socket fitted over the residual limb, a structural component system affixed to the socket that may include a pylon and articulated replacement joints (such as a knee or ankle) depending on the patient and location of the amputation, and knee cuffs, belts or other systems to secure the device to the body. A prosthetic sock or liner is typically worn over the residual limb within the socket to cushion the area of contact, and, in some cases, realistic-looking skin is provided over the structural components for aesthetic reasons.

As shown in FIG. 1, the socket 22 receives the wearer's residual limb. The socket 22 is typically a fiberglass or other composite shell molded to conform to the user's residual limb. The socket 22 is seated on a choke adapter 24. Choke adapter 24 includes an array of branches 26 that grip the socket 22. Typically, the branches 26 are integrally and permanently molded inside the socket 22. The permanently-attached choke adapter 24 positions a screw-tightenable C-ring clamping collar 28 directly beneath the socket 22. In addition to being screw-tightenable in a clamping manner, collar 28 is internally threaded. A pyramid receptacle 40 includes an externally-threaded end that is screw-threaded into the collar 28 of choke adapter 24. The other end of pyramid receptacle 40 screw-clamps to a pyramidal link-plate 10 mounted to the knee-joint assembly for transfemoral (above-knee) patients. Alternatively, the other end of pyramid receptacle 40 screw-clamps to a pyramidal coupling on a foot assembly for transtibial (below the knee) patients. A plurality of screws may be inserted through holes 18 in the pyramidal link-plate 10 to secure it to the respective prosthetic limb components fastened there beneath (an articulating knee joint and foot are shown). The conventional pyramidal link-plate 10 and the conventional pyramid receptacle 40 are primarily based upon the "Adjustable Link" described in U.S. Pat. No. 3,659,294 to Glabiszewski, the disclosure of which is incorporated herein by reference.

Specifically, and as shown in FIG. 1, the conventional pyramidal link-plate 10 wields a frustopyramidal, four-sided boss 12 projecting from a dome-shaped, or a spherically-convex-shaped base 14, which in turn projects from a plate member 16. The plate member 16 will typically include four screw- or bolt-receiving, through-holes 18 corresponding to a standard (within the industry) four-hole pattern. The pyramid receptacle 40 fits over the four-sided boss 12, is angularly adjusted as desired, and then screw-clamps by set screws 45 onto the four-sided boss 12 to maintain the alignment. In fitting prosthetic limbs to patients, it is often necessary to modify and adjust the alignment and orientations of the various prosthetic limb components with respect to each other during the initial fitting or after the patient has worn the prosthetic limb for a period of time. The four-sided boss 12 engagement with the pyramid receptacle 40 allows the prosthetist to adjust the angular orientation before fixing it in place. However, the foregoing configuration requires several components and takes up considerable linear space. It is critically necessary to preserve the same pivoting axes on the prosthetic side, at the same height, as would have existed with the non-prosthetic limb. However, with certain transfemoral amputees, the allocable distance between the distal end of the patient's residual limb and the patient's natural knee center is very short, and it is difficult to size the foregoing plate member 16, and pyramid receptacle 40 so that the combined length of the components between a prosthetic limb socket 22 and the prosthetic knee joint 60 is equal to the distance between the distal end of the patients residual limb and the patient's natural knee center. If the combined length of the coupling components is too long the knee center on the prosthetic side will be too low, thus causing gait deviation.

The same issues arise for transtibial (below the knee) patients because the very same length requirements apply beneath the distal end of the residual limb and the prosthetic foot.

Accordingly, there is a need for a prosthetic-limb coupling-socket adapter assembly suitable for both transfemoral (above the knee) patients as well as transtibial (below the knee) patients, that affords rotatable (angular) adjustment for the prosthetic limb or foot, yet does not significantly increase the profile or length of the attachment of the interconnection components.

SUMMARY OF THE INVENTION

Accordingly, it is an object of the present invention to provide a prosthetic-limb coupling-socket adapter assembly that substantially recesses the pyramid receptacle into the C-ring clamping collar of the choke adapter, so as not to significantly increase the profile length of the interconnection between socket and knee joint.

It is another object to provide a prosthetic-limb coupling-socket adapter assembly as above that facilitates angular adjustment of the prosthetic limb or foot before affixing it in place.

It is another object to provide a shock/torsion-control prosthetic-limb coupling-socket adapter with all the foregoing qualities.

The above and other objects, features and advantages of the present invention will become readily apparent from the following detailed description thereof which is to be read in connection with the accompanying drawings, in which an adapter is described for coupling a prosthetic limb or foot to a transtibial or transfemoral socket. The adapter is formed with a cylindrical neck capped by a disk-like flange. The neck is opened at both ends and defined by external screw-threads along its entire length for screw-insertion into an existing choke adapter, and a radial array of internally threaded screw-holes are journalled sidelong into the neck section through and interrupting the external screw-threads around said neck section. The disk section is integrally and coaxially joined on one side to the neck section, but has a larger diameter. The other (outward facing) side of the disk section is defined by a concave face formed with a central cavity therein, the cavity extending into and forming a chamber within the neck section for insertion of the pyramidal post of a conventional link-plate. A plurality of headless threaded set screws are inserted into the radial array of threaded screw-holes for locking engagement with the post of the conventional link-plate.

An alternate embodiment of the prosthetic-limb coupling-adapter assembly is provided which implements the concept with a shock/torsion adapter to enable limited transverse plane rotation and vertical shock absorption of the pyramidal post of the conventional link-plate, thereby reducing limb asymmetries and improving comfort leading to increased confidence and stability during gait.

The prosthetic-limb coupling-adapter assembly is suitable for both transfemoral (above the knee) patients as well as transtibial (below the knee) patients, and affords rotatable (angular) adjustment for the prosthetic limb or foot, yet minimizes the profile or length of the attachment of the interconnection components.

BRIEF DESCRIPTION OF THE DRAWINGS

Other objects, features, and advantages of the present invention will become more apparent from the following detailed description of the preferred embodiment and certain modifications thereof, in which.

DETAILED DESCRIPTION OF THE PREFERRED EMBODIMENTS

The present invention is a pyramid receptacle for a prosthetic-limb (or foot) coupling assembly that still affords rotatable (angular) adjustment for the prosthetic limb, yet does not significantly increase the profile or length of the attachment of the interconnection components.

Figure 1:
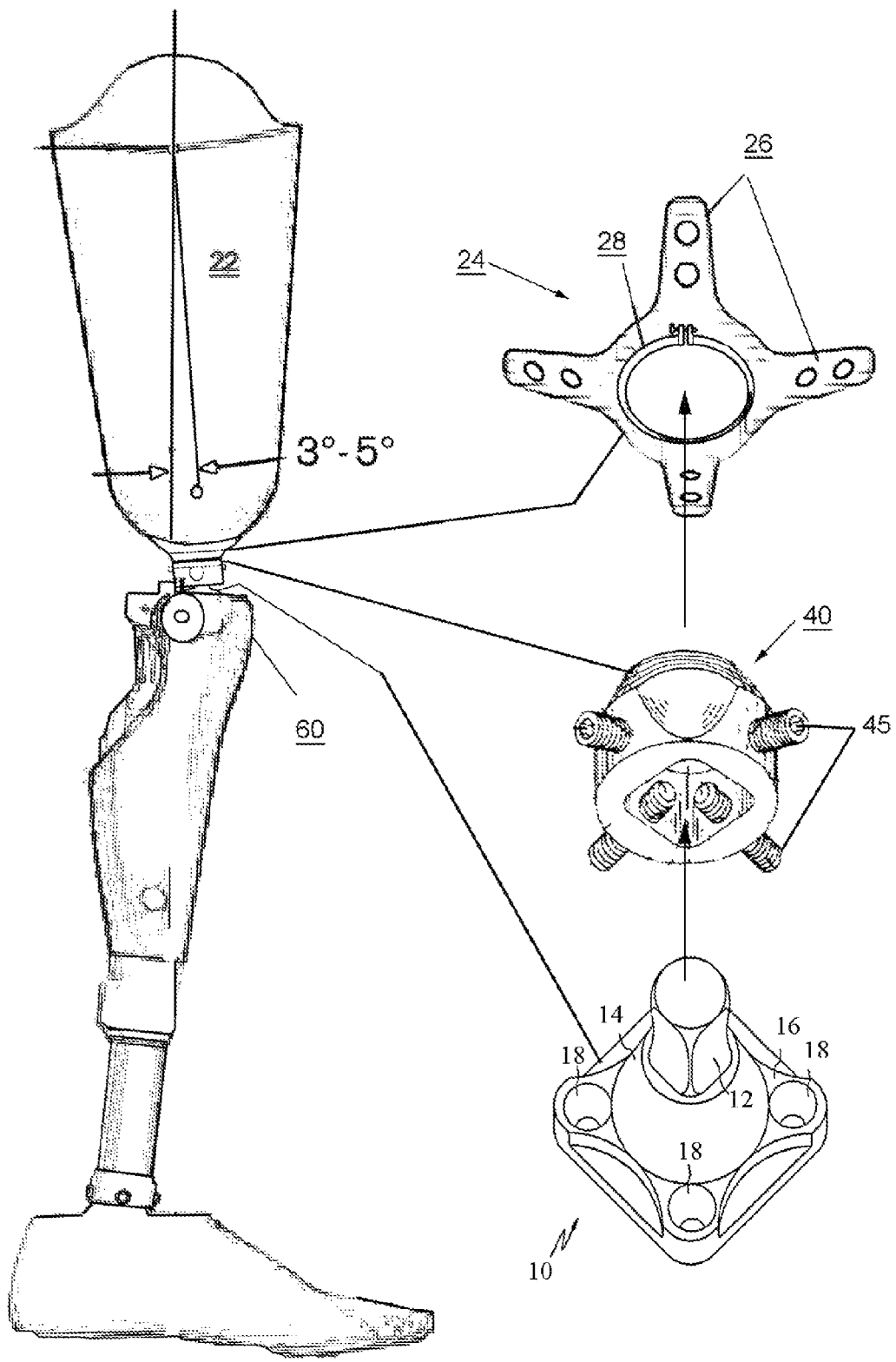
FIG. 1 is a perspective view of a prior art prosthetic-limb coupling-socket adapter assembly, with inset showing exploded primary components.
Figure 2:
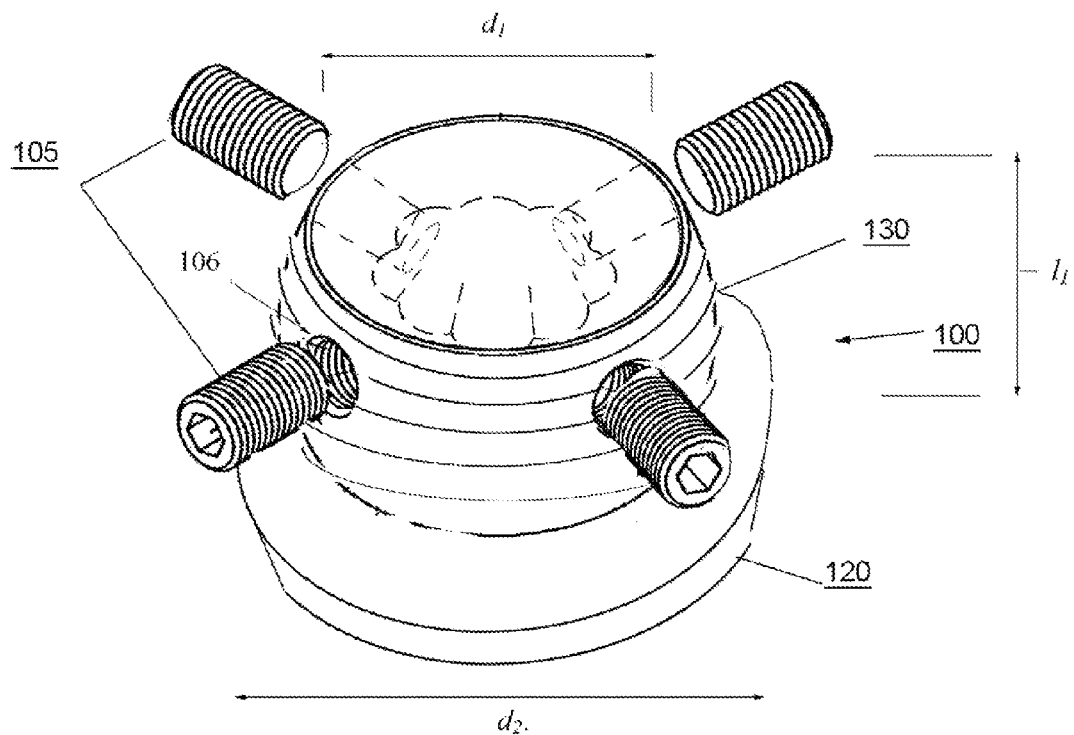
FIG. 2 is a perspective view of a pyramid receptacle 100 according to the present invention, seen from the top.
Figure 3:
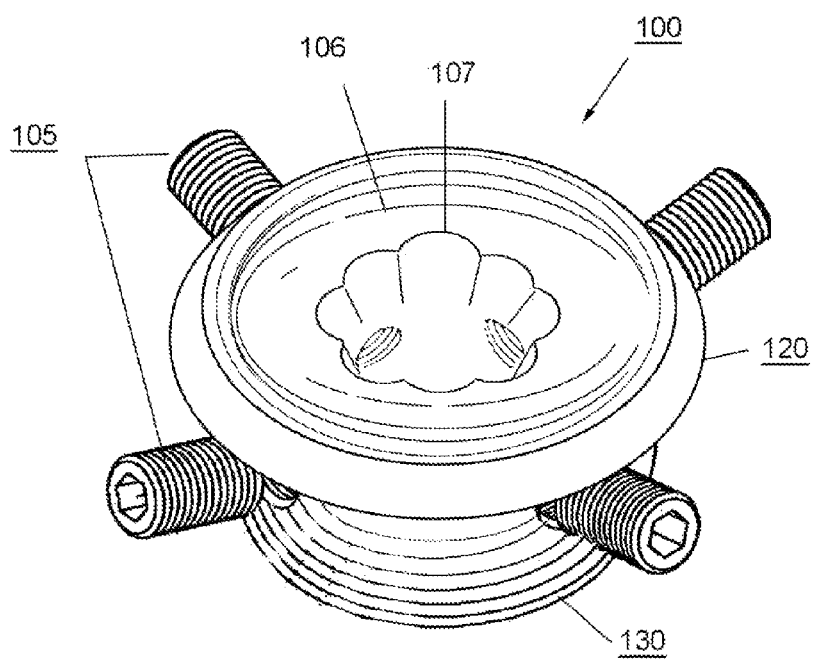
FIG. 3 is a perspective view of a pyramid receptacle 100 according to the present invention, seen from the bottom.

FIGS. 2-3 are perspective views of the pyramid receptacle 100 according to an embodiment of the present invention. Pyramid receptacle 100 comprises a unitary precision-machined part formed with a hollow threaded neck section 130 flanged by a larger-diameter disk 120. The hollow threaded neck section 130 is a open-ended cylindrical section having an external first diameter $d_1$, length $l_1$, and defined by external screw-threads along its entire length $l_1$. Neck section 130 protrudes upward to a flat-topped circular face, and is peripherally sized to fit within the C-ring clamping collar 28 of choke adapter 24 (FIG. 1), and is screw-threaded and clamped therein.

In the preferred embodiment disk 120 is integrally formed with neck section 130 but extends outward there from, having a slightly larger diameter $d_2$. However, one skilled in the art should understand that disk 120 is not an essential part of the invention and can be eliminated if desired. The bottom face of the disk 120 is formed with a concave surface 109 to form a bearing surface against the convex portion 14 of the conventional pyramidal link-plate 10 of FIG. 1. At the center of the concave surface 109 a central aperture 107 is defined and opens outward, preferably in an eight-petal flower configuration as illustrated, to receive and seat the frustopyramidal four-sided boss 12 projecting from the pyramidal link-plate 10 (of FIG. 1). A plurality of headless threaded set screws 105 are inserted into a radial array of threaded screw-holes 106, the screw-holes being journalled into the sides of the hollow threaded neck section 130 and penetrating into the hollow cavity of central aperture 107 to bear against the frustopyramidal four-sided boss 12, selectively affixing its position.

Preferably, four (4) threaded set screws 105 are journalled into four internally screw-threaded holes 106 extending through the hollow threaded neck section 130 and into communication with the hollow interior chamber therein. As best shown in FIGS. 2 and 3, the internally-screw-threaded bore holes 106 are precision-machined in a radial array directly through the threads of the neck section 130, and are spaced from each other in a horizontal plane ninety degrees apart. It is important that the internally-screw-threaded bore holes 106 be precision-tapped through the threads of the neck section 130 so as not to introduce any discontinuities into the helical screw threads of the neck section 130. This is essential to eliminate incongruities when screw-inserting the neck section 130 into the clamping collar 28 of choke adapter 24 as shown in FIG. 1. The axis of each bore hole 106 is preferably angled upward slightly (with regard to FIG. 2) from the horizontal plane at acute angles of about 2-10 degrees, so as to converge inward and upward at a camber. The length of the headless threaded set screws 105 is calculated so that they fully reside within the neck section 130 when abutting the boss 12 projecting from the pyramidal link-plate 10 (of FIG. 1).

The shape and flowered petal-configuration of the central aperture 107 cooperates with the frustopyramidal shape of boss 12 to allow the prosthetist to adjust the angular orientation of the of the pyramid receptacle 100 before locking it in position with set screws 105. So long as the set screws 105 remain flush or recessed below the threads of the threaded neck section 130 even when locked against the four-sided boss 12, the hollow threaded neck section 130 of pyramid receptacle 100 can still be screwed into the C-ring clamping collar 28 of choke adapter 24 as shown in FIG. 1.

This careful machining of threaded radial holes 106 for the plurality of set screws 105 directly through the hollow threaded neck section 130, and ensuring that the set screws 105 stay flush or recessed when fully tightened effectively halves the length of the pyramid receptacle 100 when compared to the prior art. This takes on special significance because it facilitates angular adjustment of the prosthetic limb before affixing it in place, yet minimizes the profile length of the interconnection between socket and knee joint. Once the pyramid receptacle 100 is attached on one side to the four-sided boss 12 at the proper camber, the entire lower leg assembly can be secured (clamped and/or threaded) in the clamping collar 28 to affix the pyramid receptacle 100 to the socket.

The above-described invention may be used for transtibial (below the knee) patients, where a similar pyramidal link-plate 10 attaches a prosthetic foot. All the same advantages accrue because the very same length requirements apply between the distal end of the residual limb and the prosthetic foot.

Figure 4:
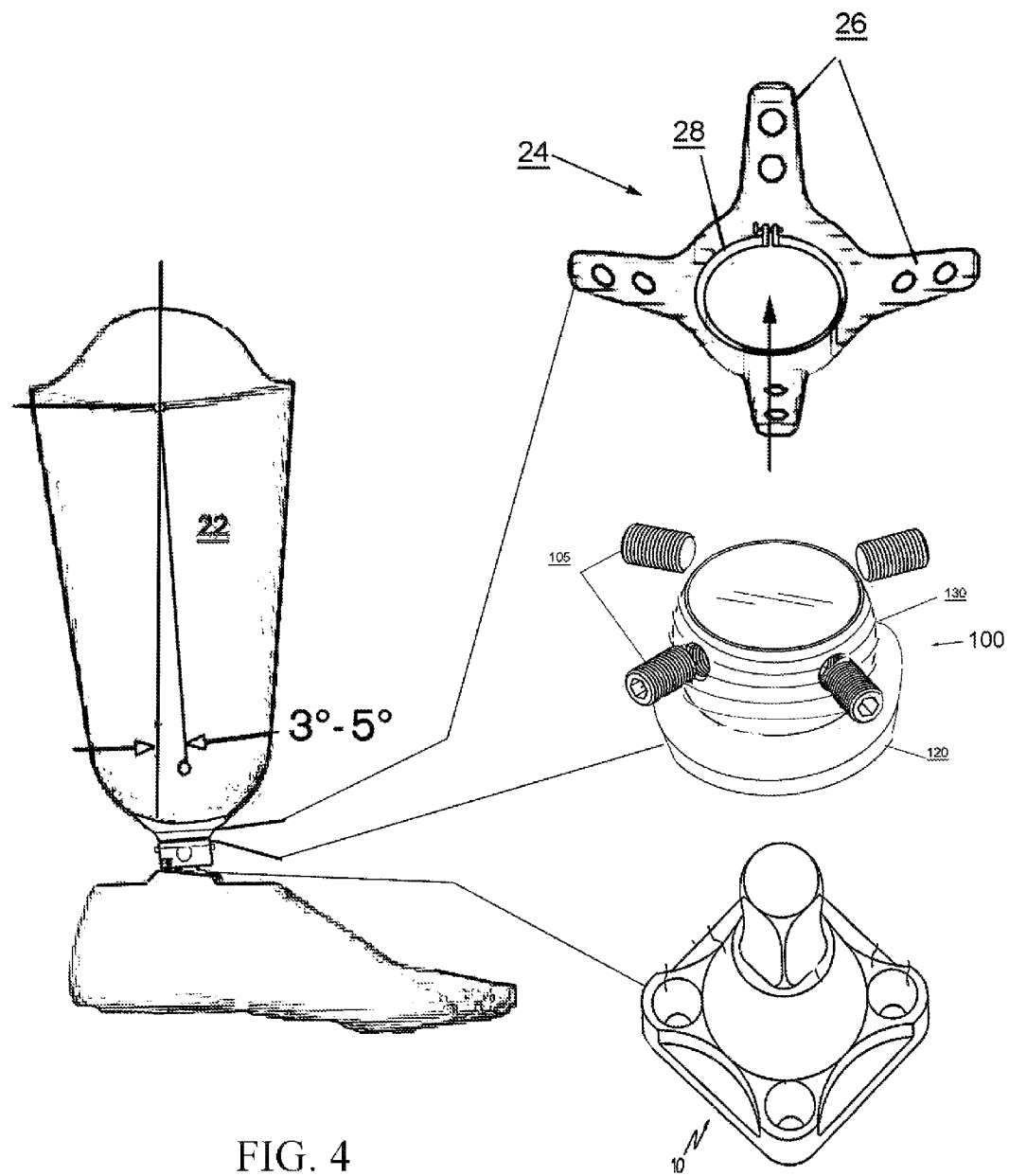
FIG. 4 is a pyramid receptacle 100 according to the present invention used for a transtibial (below the knee) patient in coupling to a foot assembly.

FIG. 4 illustrates the pyramid receptacle 100 used for a transtibial (below the knee) patient in coupling to a foot assembly.

The concept of the present invention may also be implemented as a shock/torsion adapter. Integrating a shock/torsion adapter into the pyramid receptacle 100 enables limited transverse plane rotation and vertical shock absorption of the pyramidal link-plate 10 and can help reduce limb asymmetries and improve comfort leading to increased confidence and stability during gait.

Figure 5:
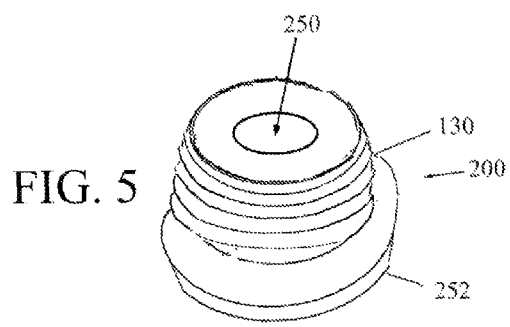
FIG. 5 is a perspective top view of an embodiment of a pyramid adapter 200 according to the present invention which incorporates a torsion adapter.

FIG. 5 is a perspective top view of an embodiment of a pyramid adapter 200 according to the present invention which incorporates an integral shock/torsion adapter for providing limited angular rotation against a predetermined resistance, and also vertical load absorption. The combination of rotation/resistance and vertical load absorption affords more natural movement when used by transtibial as well as transfemoral amputees reducing stress forces against the residual limb. The pyramid adapter 200 is exteriorly similar in form and function to that of FIGS. 1-4, and includes an internal rotation spindle 250 to allow limited rotation and shock absorption from a home position against a controlled resistance that biases the rotation spindle 250 back to the home position. The pyramid adapter 200 also provides a vertical shock absorption characteristic by damping compression/vertical loading.

Figure 6:
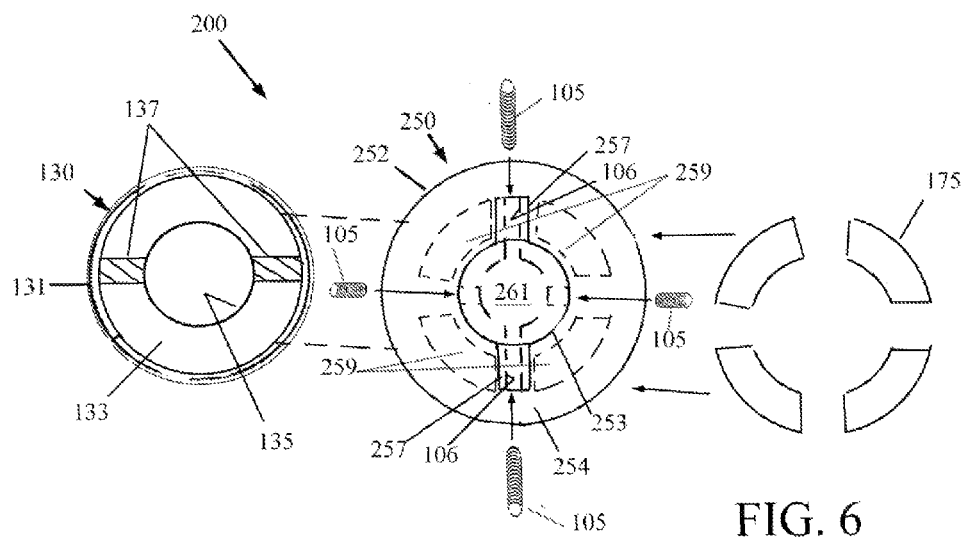
FIG. 6 is a top view of the disassembled pyramid adapter 200 of FIG. 5.
Figure 7:
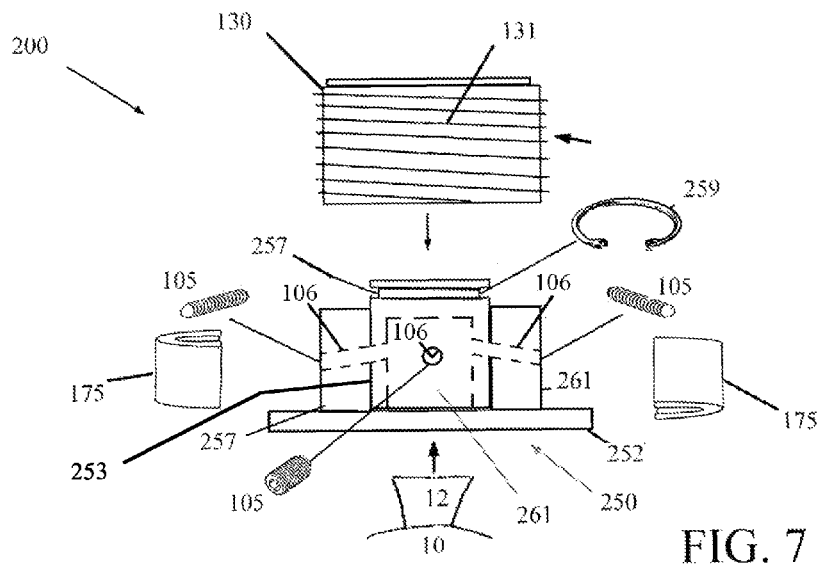
FIG. 7 is a side view of the disassembled pyramid adapter 200 of FIG. 5.

FIG. 6 is a top view of the disassembled pyramid adapter 200 of FIG. 5, and FIG. 7 is a side view. The hollow threaded neck section 130 is formed as a hollow annular sleeve open at the lower end and partially capped by an annular flange 133 at the upper end, flange 133 being defined by a smaller diameter circular central aperture 135. The hollow threaded neck section 130 is also formed with a pair of opposing inwardly-directed radial partitions 137, e.g., solid walls running top to bottom and spanning the interior of the hollow threaded neck section 130 from the surface of its inner cylindrical wall to the central aperture 135. As above the cylindrical exterior wall 131 is exteriorly threaded from top to bottom as per FIGS. 1-4. The threaded neck section 130 fits down overtop the rotation spindle 250. The spindle 250 is formed as a hollow cylindrical stem 253 rising centrally from a larger-diameter flange 252 at the bottom. The spindle 250 is also formed with a pair of opposing outwardly-directed radial partitions 257, e.g., solid walls running approximately two-thirds the height of spindle 250 from the bottom flange 252 toward the top. The hollow threaded neck section 130 fits overtop the stem 253 and rotates thereon, stem 253 protruding outward through circular top aperture 135. The distal top end of stem 253 is formed with an annular slot 257 for accepting a C-ring 259, C-ring 259 thereby retaining the hollow threaded neck section 130 on the stem 253 but free to rotate. With the hollow threaded neck section 130 mounted on the spindle 250, the radial partitions 257 of spindle 250 span the interior to the inner walls of threaded neck section 130, and the radial partitions 137 of the hollow threaded neck section 130 span to the stem 253 of spindle 250. The two pairs of diametric partitions 137, 257 effectively divide the interior space into quadrants and yet remain free to rotate relative to each other. The space between the partitions 137, 257 define four radially-spaced pockets 259 for seating a corresponding plurality of semi-circular torsion and vertical shock limiters 175. The torsion/shock limiters 175 are elastic (such as silicon rubber, urethane or other resilient material), and are sandwiched between the inner wall of neck section 130 and stem 253, held captive between the partitions 137, 257 for rotation and held captive between annular flange 133, and bottom flange 252 allowing for vertical load absorption. In the preferred embodiment, four crescent-shaped torsion/shock limiters 175 are used, one in each pocket 259 in each quadrant. The elasticity of the torsion/shock limiters 175 is chosen to allow a predetermined limited degree of rotational freedom and load absorption of the hollow threaded neck section 130 relative to the stem 253. Thus, when the threaded neck section 130 is rotated or compressed relative to the stem 253, all four torsion/shock limiters 175 become compressed between partitions 137 and partitions 257 for rotation and flange 133 and 252 for load absorption. In addition, the thickness of the torsion/shock limiters 175 is chosen to impart predetermined bias between the hollow threaded neck section 130 relative to the bottom flange 252. This way, the pyramid adapter 200 also provides a vertical shock absorption characteristic by damping compression/vertical loading.

This affords limited rotation and shock absorption of spindle 250 from a home position against a controlled elastic resistance, to a maximum angular rotation and load absorption, with a bias back to the home position.

The stem 253 is hollow and open downward to accept the pyramidal link-plate 10 of FIG. 1 inserted therein from beneath. The stem 253 is further defined by four radially-oriented threaded screw-bores 106 leading axially inward through the stem 253 into the hollow for securing the pyramidal link-plate 10 therein. Two of the threaded screw-bores 106 lead axially inward through the partitions 257 in spindle 250, and two lead axially inward directly through the spindle 250 between the partitions 257, the four threaded screw-bores 106 being angularly offset 90 degrees. All of the threaded screw-bores accept insertion of set screws 105, two set screws being slightly longer than the other two to fully traverse the partitions 257. As shown, when fully inserted the sets screws 105 remain recessed in the stem 253.

The frustopyramidal four-sided boss 12 projecting from the pyramidal link-plate 10 of FIG. 1 is inserted from beneath into the hollow cavity 261 of the stem 253 and is secured thereto by the headless threaded set screws 105. The hollow threaded neck section 130 is then inserted onto the stem 253 of the spindle 250 and is secured thereon by C-clip 259. The entire pyramid adapter 200 may then be screwed into the C-ring clamping collar 28 of choke adapter 24 as shown in FIG. 1.

Figure 8:
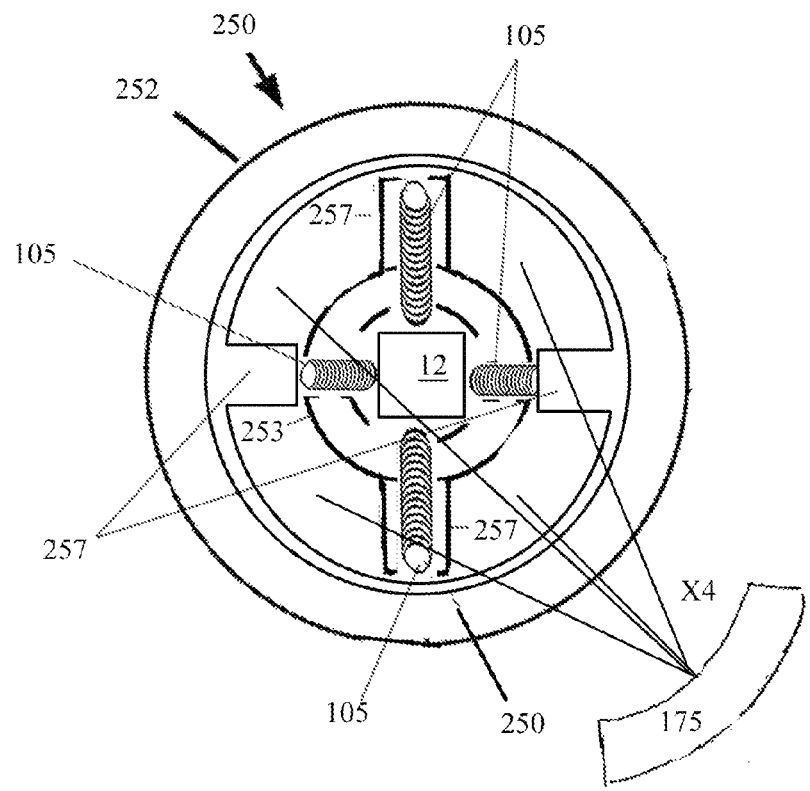
FIG. 8 is a side view top cut-away view of the spindle 130 with cylindrical stem 253.

FIG. 8 is a side view top cut-away view of the spindle 250 with cylindrical stem 253 and the frustopyramidal four-sided boss 12 projecting from the pyramidal link-plate 10 of FIG. 1 inserted therein and secured thereto by the headless threaded set screws 105. Upon rotation, the torsion/shock limiters 175 are squeezed between partitions 137 and partitions 257. Upon vertical load the torsion/shock limiter 175 are compressed between flanges 133 and flange 252.

Figure 9:
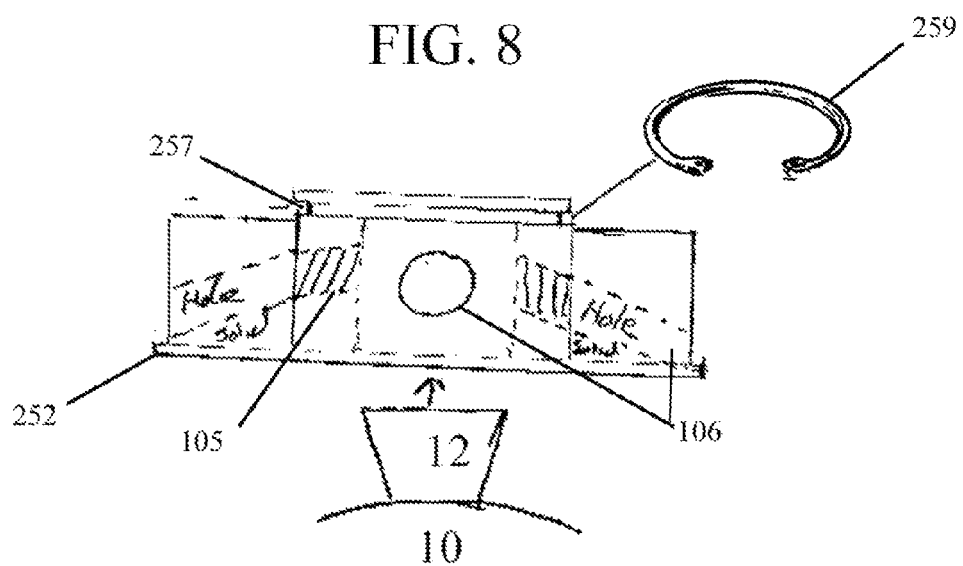
FIG. 9 is a side cut-away view of the spindle 250 as in FIG. 8.

FIG. 9 is a side cut-away view of the spindle 250 as in FIG. 8 illustrating ingress of the headless screws 105 through tapped screw holes 106. This configuration provides an integral shock/torsion adapter with limited angular rotation and shock absorption against a predetermined resistance, and still substantially recesses the pyramid receptacle 200 into the C-ring clamping collar of the choke adapter, so as not to significantly increase the profile length of the interconnection between socket and knee joint.

It should now be apparent that the above-described prosthetic-limb coupling-adapter is suitable for both transfemoral (above the knee) patients as well as transtibial (below the knee) patients, and in both cases affords rotatable (angular)

adjustment for the prosthetic limb or foot, yet minimizes the profile or length of the attachment of the interconnection components.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. In combination with a choke adapter attached to a prosthetic socket, and a pyramidal link-plate coupled to prosthetic limb, a pyramid receptacle for connecting said pyramidal link-plate to said choke adapter, said pyramid receptacle comprising:
    a unitary annular member formed with hollow cylindrical neck section defined by external screw threads, and an internal cavity opening outward from an end of said neck section, and a plurality of internally threaded screw-bores entering said cylindrical neck section through said external screw threads and penetrating into said internal cavity; and
    a plurality of headless threaded set screws each journalled into a corresponding one of said plurality of internally threaded screw-bores, each of said plurality of threaded set screws having a length dimensioned to extend at one end into said internal cavity when recessed fully inside said corresponding threaded screw-bore.

2. The pyramid receptacle according to claim 1, wherein said unitary annular member further comprises a disk flange at one end of said cylindrical neck section, the disk flange having a larger-diameter than said cylindrical neck section.

3. The pyramid receptacle according to claim 2, wherein said disk flange is formed with a concave face having a central aperture therein.

4. The pyramid receptacle of claim 1, wherein said plurality of headless threaded set screws consists of four headless threaded set screws, and said plurality of internally threaded screw-bores consists of four internally threaded screw-bores.

5. The pyramid receptacle of claim 1, wherein said plurality of internally threaded screw-bores are angled through said neck section at a camber angle.

6. The pyramid receptacle of claim 4, wherein said four internally threaded screw-bores are radially spaced about said neck section at 90 degree intervals.

7. An adapter for coupling a prosthetic to a socket, comprising:
    a cylindrical neck open at both ends and defined by external screw-threads along its entire length, and a radial array of internally threaded screw-holes journalled sidelong into said neck section through and interrupting said external screw-threads around said neck section;
    a disk section integrally and coaxially joined on one side to said neck, said disk section having a diameter larger than that of said neck section, and having an opposing side defined by a concave face formed with a central cavity therein and extending into said neck section;
    a plurality of headless threaded set screws inserted into said radial array of threaded screw-holes.

8. The adapter of claim 7, wherein said radial array of internally threaded screw-holes further comprises four screw holes journalled sidelong into said neck section through and interrupting said external screw-threads around said neck section.

9. The adapter of claim 7, wherein said central cavity of said disk section opens outward in an eight-petal flower configuration.

10. The adapter of claim 7, wherein said internally-screw-threaded bore holes are precision-tapped through the external threads of the neck section so as not to introduce any discontinuities.

11. The adapter of claim 7, wherein said internally-screw-threaded bore holes are angled upward at a camber.

12. The adapter of claim 11, wherein said camber angle is within a range of between 2-10 degrees offset from horizontal.

13. The adapter of claim 7, wherein said threaded set screws are headless.

14. The adapter of claim 13, wherein said headless threaded set screws may be fully submerged into said internally-screw-threaded bore holes.

* * * * *